United States Patent [19]
Qvist et al.

[11] Patent Number: 6,117,646
[45] Date of Patent: *Sep. 12, 2000

[54] ASSAYING PROTEIN FRAGMENTS IN BODY FLUIDS

[75] Inventors: Per Qvist, Klampenborg; Martin Bonde, Lyngby, both of Denmark

[73] Assignee: Osteometer Biotech A/S, Herlev, Denmark

[*] Notice: This patent issued on a continued prosecution application filed under 37 CFR 1.53(d), and is subject to the twenty year patent term provisions of 35 U.S.C. 154(a)(2).

[21] Appl. No.: 09/053,521

[22] Filed: Apr. 2, 1998

Related U.S. Application Data

[63] Continuation-in-part of application No. 08/913,806, Sep. 22, 1997.

[51] Int. Cl.⁷ .................................................. G01N 33/53
[52] U.S. Cl. ...................... 435/7.93; 435/7.1; 435/7.92; 435/7.94; 435/7.95; 436/518; 436/532; 530/323; 530/326; 530/327; 530/328; 530/329; 530/356; 530/388.1; 530/389.1
[58] Field of Search .................................. 435/7.1, 7.92, 435/7.93, 7.94, 7.95; 436/518, 532; 530/323, 326, 327, 328, 329, 356, 388.1, 389.1

[56] References Cited

U.S. PATENT DOCUMENTS

| | | |
|---|---|---|
| 3,600,132 | 8/1971 | Goverde . |
| 4,312,853 | 1/1982 | Timpl . |
| 4,504,587 | 3/1985 | Timpl et al. . |
| 4,628,027 | 12/1986 | Gay . |
| 4,778,768 | 10/1988 | Heinegard et al. . |
| 4,973,666 | 11/1990 | Eyre . |
| 5,001,225 | 3/1991 | Taylor . |
| 5,140,103 | 8/1992 | Eyre . |
| 5,300,434 | 4/1994 | Eyre . |
| 5,320,970 | 6/1994 | Eyre . |
| 5,455,179 | 10/1995 | Eyre . |
| 5,472,884 | 12/1995 | Eyre . |
| 5,473,052 | 12/1995 | Eyre . |
| 5,532,169 | 7/1996 | Eyre . |
| 5,576,189 | 11/1996 | Eyre . |
| 5,607,862 | 3/1997 | Eyre . |

FOREIGN PATENT DOCUMENTS

| | | |
|---|---|---|
| 0 298 210 | 1/1989 | European Pat. Off. . |
| 0 339 443 | 11/1989 | European Pat. Off. . |
| 0 394 296 | 10/1990 | European Pat. Off. . |
| 0 424 428 | 5/1991 | European Pat. Off. . |
| 0 465 104 | 1/1992 | European Pat. Off. . |
| 0 502 928 | 9/1992 | European Pat. Off. . |
| 0 505 210 | 9/1992 | European Pat. Off. . |
| 42 25 038 | 2/1994 | Germany . |
| 2 205 643 | 5/1987 | United Kingdom . |
| WO 83/04104 | 11/1983 | WIPO . |
| WO 88/08980 | 11/1988 | WIPO . |
| WO 89/04491 | 5/1989 | WIPO . |
| WO 89/12824 | 12/1989 | WIPO . |
| WO 90/04417 | 5/1990 | WIPO . |
| WO 90/08195 | 7/1990 | WIPO . |
| WO 91/08478 | 6/1991 | WIPO . |
| WO 91/09114 | 6/1991 | WIPO . |
| WO 92/21698 | 12/1992 | WIPO . |
| WO 94/03813 | 2/1994 | WIPO . |
| WO 94/14844 | 7/1994 | WIPO . |
| WO 95/04282 | 2/1995 | WIPO . |
| WO 95/08115 | 3/1995 | WIPO . |
| WO 96/30765 | 10/1996 | WIPO . |

OTHER PUBLICATIONS

International Search Report dated Feb. 15, 1995 of Int'l Appl. No. PCT/DK94/00348.

Ala–Kokko et al., 1989, "Structure of cDNA clones coding for the entire preproα1(III) chain of human type III procollagen", *Biochem. J.* 260:509–516.

Ala–Kokko et al., 1990, "Single base mutation in the type II procollagen gene (COL2A1) as a cause of primary osteoarthritis associated with a mild chondrodysplasia", *Proc. Natl. Acad. Sci.* 87:6565–6568.

Baldwin et al., 1989, "Structure of CDNA clones coding for human type II procollagen", *Biochem. J.* 262:521–528.

Beardsworth et al., 1990, "Changes with age in the urinary excretion of lysyl– and hydroxylysylpyridinoline, two new markers of bone collagen turnover", *J. Bone Miner. Res.* 5:671–676.

Bernard et al., 1983, "Nucleotide Sequences of Complementary Deoxyribonucleic Acids for the Proα1 Chain of Human Type I Procollagen. Statistical Evaluation of Structures That Are Conserved during Evolution", *Biochemistry* 22:5213–5223.

Black et al., 1988, "Quantitative analysis of the pyridinium crosslinks of collagen in urine using ion–paired reversed–phase high–performance liquid chromatography", *Ana. Biochem.* 169:197–203.

Black et al., 1989, "Urinary excretion of the hydroxypyridinium cross links of collagen in patients with rheumatoid arthritis", *Annals of the Rheumatic Diseases* 48:641–644.

Bonde et al., 1994, "Immunoassay for Quantifying Type 1 Collagen Degradation Products in Urine Evaluated", *Clin. Chem.* 40(11):2022–2025.

(List continued on next page.)

Primary Examiner—Jeffrey Stucker
Attorney, Agent, or Firm—Pennie & Edmonds, LLP

[57] ABSTRACT

Type I collagen degradation products are assayed in a body fluid by conducting a competition immunoassay in which sample molecules compete with a peptide or isomerized peptide in binding to an immunological binding partner for the peptide or isomerized peptide respectively, wherein the peptide or isomerized peptide comprises the amino acids AHDGGR optionally extended at the N-terminal end with one or more amino acids that do not form a contiguous sequence with AHDGGR in type 1 collagen, and wherein D represents aspartic acid or β-aspartic acid. The peptide $C(X)_n$ AHDGGR, where X is any amino acid and n is preferably from 4 to 6 is provided for use in such assays and in diagnostic assay kits.

7 Claims, 5 Drawing Sheets

OTHER PUBLICATIONS

Bonde et al., 1995, "Measurement of Bone Degradation Products in Serum Using Antibodies Reactive with an 8 Amino Acid Sequence of the C–Telopeptides of Type I Collagen", *J. of Bone and Min. Res.* 10:1–Abstract S481.

Brennan et al., 1993, "Spontaneous degradation of polypeptides at aspartyl and asparaginyl residues: Effects of the solvent dielectric", *Protein Science* 2:331–338.

Capecchi et al., "Critical examination of a method for the analysis of α and ω linkages in peptides containing aspartic acid and glutamic acid", *J. Org. Chem.* 48:2014–2021.

Christiansen et al., "Prediction of future fracture risk", eds, Proceedings 1993. Fourth International Symposium on Osteoporosis, Hong Kong. Osteopress Aps 1993; pp. 52–54.

Chu et al., 1984, "Human proα1(I) collagen gene structure reveals evolutionary conservation of a pattern of itrons and exons", *Nature* 310:337–340.

Click et al., 1970, "Isolation and Characterization of the Cyanogen Bromide Peptides from the α1 and α2 Chains of Human Skin Collagen", *Biochemistry* 9:4699–4706.

de Wet et al., 1987, "Organization of the Human Pro–α2(I) Collagen Gene", *J. Biol. Chem.* 262:16032–16036.

Delmas et al., 1986, "Serum Bone GLA–Protein in Growth Hormone Deficient Children", *J. Bone Min. Res.* 1:333–337.

Delmas, P.D., 1990, "Biochemical markers of bone turnover for the clinical assessment of metabolic bone disease", *Metabolic Bone Dis.* 19:1–18.

Dickson et al., 1993, "Pyridinolines and Cross–linked Type I Collagen N–telopeptides as Markers of Bone Metastases in Breast Cancer", 15$^{th}$ Annual Mtg of the Amer. Soc. for Bone & Min. Res., Tampa, Fl., Sep., 8:S288, Abstr. 686.

Dodge et al., 1989, "Immunohistochemical Detection and Immunochemical Analysis of Type II Collagen Degradation in Human Normal, Rheumatoid, and Osteoarthritic Articular Cartilages and in Explants of Bovine Articular Cartilage Cultured with Interleukin 1", *J. Clin. Invest.* 83:647–661.

Eyre et al., 1984, "Quantitation of Hydroxypyridinium Crosslinks in Collagen by High–Performance Liquid Chromatography", *Analytical Biochemisty* 137:380.

del Pozo et al., 1986, "Binding of 1–anilinoaphthalene–8–sulfonic acid to type I collagen" *Int. J. Pept. Protein Res.* 28:173–178.

Eyre et al., 1988, "Identification of urinary peptides derived from cross–linking sites in bone collagen in Paget's disease", *J. of Bone & Mineral Res* 3:S210, Abstr.565.

Eyre, D.R., 1984, "Cross–linking in Collagen and Elastin", *Ann. Rev. Biochem.* 53:717–748.

Eyre, D.R., 1994, "New Molecular Markers of Bone Metabolism", Therapeutic Research (Symposium) 15(2):532–535.

Fledelius et al., 1994, "Estimation of Bone Resorption Using Monoclonal Antibodies to Human Type I Collagen", *Am. Soc. of Bone and Min. Res.,* Abst. C344.

Fujimoto, D., 1980, "Evidence for natural existence of pyridinoline crosslink in collagen", *Biochem. & Biophys. Res. Comm.* 93:948–953.

Fujimoto et al., 1983, "Analysis of pyridinoline, a cross–linking compound of collagne fibers, in human urine", *J. Biochem.* 94:1133–1136.

Furthmayr, H., 1982, "Immunization procedures, isolation by affinity chromatography, and serological and immunochemical characterization of collagen specific antibodies", *Immunochemistry of the extracellular matrix,* H. Furthmayr (ed.), CRC Press, Vol. 1, Chap. 11, pp. 143–178.

Galletti et al., 1995, "Protein damage and methylation–mediated repair in the erythrocyte" *Biochem. J.* 306:313–325.

Garnero et al., "Assessment of Bone Resportion with a New Marker of Collagen Degradation in Patients with Metabolic Bone Disease", *J. Clin. Endo. and Met.* 79(3):780–785.

Garnero et al., 1994, "Different Effects of Bisphosphonate and Estrogen therapy on the Excretion of Free and Peptide–Bound Crosslinks", *Amer. Soc. of Bone and Min. Res.,* Abst. 134.

Gertz et al., 1994, "Monitoring bone resorption in early postmenopausal women by an immunoassay for cross–linked collagen peptides in urine", *J. of Bone & Min. Res.* 9(2):135–142.

Gunja–Smith et al, 1981 "Collagen cross–linking compounds in human urine", *Biochem. J.* 197:759–762.

Hanson et al., 1992, "A specific immunoassay for monitoring human bone resorption: Quantitation of type I collagen cross–linked N–telopeptides in urine", *J. of Bone & Min. Res.* 7:1251–1258.

Hassager et al., 1994, "The carboxy–terminal pyridinoline cross–linked telopeptide of type I collagen in serum as a marker of bone resorption: The effect of nandrolone decanoate and hormone replacement therapy", *Calcif. Tissue Int.* 54:30–33.

Henkel et al., 1987, "Characterisation of a type–I collagen trimeric cross–linked peptide from calf aorta and it cross–linked structure", *Eur. J. Biochem.* 165:427–436.

Ishikawa, E., 1983, "Enzyme–Labeling of Antibodies and their Fragments for Enzyme Immunoassay and Immunohistochemical Staining", *Journal of Immunoassay* 4(3):209–327.

Janeczko et al., 1989, "Nucleotide and amino acid sequences of the entire human α1 (III) collagen", *Nucl. Acids Res.* 17:6742.

Kiviriko, K.I., 1979, "Urinary Excretion of Hydroxyproline in Health and Disease", *Int. Rev. Connect. Tissue Res.* 5:93–163.

Krane et al., 1981, "Organic Matrix Defects in Metabolic and Related Bone Diseases", *Develop. Biochem.* 22:185–194.

Kruger–Franke, 1991, "Pyridinoline–containing collagen degradation products in the urine of patients with osteoarthrosis of the hip joint", *Z. Rheumatol.* 50:323–327 (German with English Translation).

Kuboki et al., 1981, "Location of the intermolecular cross–links in bovine dentin collagen, solubilization with trypsin and isolation of cross–link peptides containing dihydroxylysinonorleucine and pyridinoline", *Biochem. & Biophys. Res. Comm.* 102:119–126.

Kuhn, K., 1982, "Chemical Properties of Collagen", *Immunochemistry of the Extracellular Matrix,* H. Furthmayr (ed.), CRC Press, 1(1)1–29.

Kuhn, K., 1987, "The Classical Collagens: Types I, II, and III", *Structure & Function of Collagen Types,* Mayne & Bergeson (eds.), Academic Press, pp. 1–42.

Kuypers et al., 1992, "Identification of the loci of the collagen–associated Ehrlich chromogen in type I collagen confirms its role as a trivalent cross–link", *Biochem. J.* 283:129–136.

Last et al., 1990, "Biosynthesis of collagen crosslinks", *Int. J. Biochem.,* 22(6):559–564.

Lehrman et al., 1992, "Identification and Characterization of an Anti–Isoaspartic Acid Monoclonal Antibody", *Journ. Of Prot. Chem.* 11(6):657–663.

Loidl et al., 1984, "Molecular cloning and carboxyl–propeptide analysis of human type III procollagen", *Nucl. Acids. Res.* 12(24):9383–9394.

Lowensen et al., 1988, Does the chemical instability of aspartyl and asparaginyl residues in proteins contribute to erythrocyte aging?, *Blood Cells* 14:103–117.

Macek et al., 1987, "Determination of collagen degradation products in human urine in osteoarthrosis", *Z. Rheumatol.* 46:237–240.

Morein et al., 1984, "Iscom, a novel structure for antigenic presentation of membrane proteins from enveloped viruses", *Nature* 308:457–460.

Morgan et al., 1970, "A Comparative Study of Glycopeptides Derived from Selected Vertebrate Collagens", *J. Biol. Chem.* 245:5042–5048.

Niemelä, O., 1985, "Radioimmunoassays for Type III Procollagne Amino–Terminal Peptides in Humans", *Clin. Chem.* 31(8):1301–1304.

Oliyai et al., 1994, "Chemical pathways of peptide degradation. VI. Effects of the primary sequence on the pathways of degradation of aspartyl residues in model hexapeptides", *Pharm. Res.* 11(5):751–758.

Otter et al., 1988, "Type I Collagen α–1 Chain C–Telopeptide: Solution Structure Determined by 600–MHz Proton NMR Spectroscopy and Implications for Its Role in Collagen Fibrillogenesis", *Biochem.* 27:3560–3567.

Otter et al., 1989, A $^1$H and $^{13}$C NMR Study on the Role of Salt–Bridges in the Formation of a Type I R–Turn in N–Actyl–I–Asp–I–Glu–I–ys–I–Ser–NH *J. Biol. Struct. Dvp.* 7(3):455–476.

Pierard et al., 1984, "Radioimmunoassay for the Amino–Terminal Sequences of Type III Procollagen in Human Body Fluids Measuring Fragmented Precursor Sequences", *Anal. Biochem.* 141:127–136.

Qvist et al., 1994, "Use of a New Biochemical Marker (Crosslaps™) for the Estimation of Rate of Postmenopausal Bone Loss", *Am. Soc. Bone and Min. Res.* Abst. #B419.

Rennard et al., 1980, "Enzyme–linked immunoassay (Elisa) for connective tissue components", *Anal. Biochem.* 104:205–214.

Riggs et al., 1992, "The Prevention and Treatment of Osteoporosis", *New England J. of Med.* 327(9):620–627.

Risteli et al., 1986, "Radioimmunoassay for Monitoring Connective Tissue Metabolism", *Rheumatol.* 10:215–245.

Risteli et al., 1993, "Radioimmunoassay for the pyridinoline cross–linked carboxy–terminal telopeptide of type I collagen: A new serum marker of bone collagen degradation", *Clin. Chem.* 39:635–640.

Robins, S.P., 1982, "An enzyme–linked immunoassay for the collagen cross–link pyridinoline", *Biochem. J.* 207:617–620.

Robins et al., 1986, "Measurement of the cross linking compounds, pyridinoline, in urine as an index of collagen degradation in joint disease", *Annals of the Rheum. Diseases* 45:969–973.

Robins et al., 1987, "Measurement of hydroxypyridinium crosslinks of collagen as an index of bone matrix degradation", Paper, Lake Garda, Italy, p. 23, Abstr. OP45.

Rodriguiz et al., 1993, "Type I Collagen cross–linked N–Telopeptide excretion by osteopetrotic patients during interferon gamma therapy: A correlation with bone biochemical and densitometric markers", 15$^{th}$ Annual Mtg of the Amer. Soc. for Bone & Min. Res., Tampa, Fl., Sep., 8:S291, Abstr. 698.

Rohde et al., 1979, "Radioimmunoassay for type III procollagen peptide and its application to human liver disease", *Euro. Jour. of Clin. Invest.* 9:451–459.

Rohde et al., 1983, "Serum and urine analysis of the aminoterminal procollagen peptide type III by radioimmunoassay with antibody fab fragments", *Collagen Rel. Res.* 3:371–379.

Russell et al., 1981, "Biochemical Markers of Bone Turnover in Pagent's Disease", *Metab. Bone Dis. and Rel. Res.* 4 and 5, 255–262.

Sangiorgi et al., 1985, "Isolation and partial characterization of the entire human proα1(II) collagen gene", *Nucl. Acids Res.* 13(7):2207–2225.

Schröter–Kermani et al., 1990, "An Inhibition Elisa for the Quantification of Collagens Type I and Type II in Cyanogen Bromide–Digested Tissues Using Fragment–Directed Antibodies", *Immunol. Invest.* 19(5–6):476–491.

Schuppan et al., 1986, "Radioimmunoassay for the carboxy–terminal cross–linking domain of type IV (basement membrane) procollagen in body fluids", *J. Clin. Invest.* 78:241–248.

Scott, P.G., 1986, "Spectropic study of environment–dependent changes in the confirmation of the isolated carboxy–terminal telopeptide of type I collagen", *Biochem.* 25:974–980.

Seibel et al., 1989, "Urinary Hydroxy–pyridinium Crosslinks Provide Indices of Cartilage and Bone Involvement in Arthritic Diseases", *Journ. of Rheumatology* 16(7):964–970.

Singer et al., 1978, "Paget's Disease of Bone", *Metabolic Bone Disease* 2:489–575, (eds. Avioli, L.V. and Kane, S.M., Academic Press, New York.

Soinila et al., 1992, "Immunohistochemistry of Enkephalins: Models Studies on Hapten–Carrier Conjugates and Fixation Methods", *J. Hitochem. Cytochem.* (40):2:231–239.

Su et al., 1989, "Nucleotide sequence of the full length cDNA encoding for human type II procollagen", *Nucl. Acids Res.* 17:9473.

Tanka, 1992, "Urinary excretion of β–aspartylpeptide in relation to collagen catabolism", Department of Agricultural Chemistry, Utsunomiya University, pp. 26–29 (Japanese and English translation).

Tanaka, 1995, "Urinary excretion of β–aspartylpeptide in relation to collagen catabolism", *Chem. Abstr.* 122:13797, abstr. 122:131800w.

Tellerova et al., 1986, "Determination of larger urinary peptides in osteoarthrosis by high–performance liquid chromatography", *Scand. J. Rheumatol.* 15:52–56.

Uebelhart et al., 1990, "Urinary excretion of pyridinium crosslinks: a new marker of bone resorption in metabolic bone disease", *Bone and Mineral* 8:87–96.

Vikkula et al., 1989, "Structural analyses of the polymorphic area in type II collagen gene", *FEBS Lett.* 250:171–174.

Weiss et al., 1969, "The Quantitiative Relationship of Urinary Peptide Hydroxyproline Excretion to Collagen Degradation", *J. Clin. Invest.* 48:1–10.

Werkmeister et al., 1990, "Characterisation of a monoclonal antibody against native human type I collagen", *Euro. J. Biochem.,* 187:439–443.

Wu et al., 1984, "Identification of Hydroxypyridinium Cross–Linking Sites in Type II Collagen of Bovine Articular Cartilage", *Biochemistry* 23:1850–1857.

ASSAYING PROTEIN FRAGMENTS IN BODY FLUIDS

This application is a continuation-in-part of co-pending U.S. application Ser. No. 08/913,806, filed on Sep. 22, 1997, which is hereby incorporated by reference in its entirety.

INTRODUCTION

The present invention relates to the assaying of collagen or other protein degradation products and materials useful therefor.

BACKGROUND OF THE INVENTION

Osteoporosis is the most common bone disease in humans. Primary osteoporosis, accompanied by increased susceptibility to fractures, results from a progressive reduction in skeletal bone mass. It is estimated to affect 15–20 million individuals in the USA alone. Its basis is an age-dependant imbalance in bone remodeling, i.e., in the rates of formation and resorption of bone tissue.

In the USA about 1.2 million osteoporosis-related fractures occur in the elderly each year including about 538,000 compression fractures of the spine, about 227,000 hip fractures and a substantial number of early fractured peripheral bones. Between 12 and 20% of the hip fractures are fatal because they cause severe trauma and bleeding, and half of the surviving patients require nursing home care. Total costs from osteoporosis-related injuries now amount to at least $10 billion annually in the USA (Riggs, New England Journal of Medicine, 327:620–627 (1992)).

Osteoporosis is most common in postmenopausal women who, on average, lose 15% of their bone mass in the 10 years after menopause. This disease also occurs in men as they get older and in young amenorrheic women athletes. Despite the major, and growing, social and economic consequences of osteoporosis, the availability of reliable assays for measuring bone resorption rates in patients or in healthy subjects is very limited. Other disorders entailing (and correlated with) abnormalities in collagen metabolism include Paget's disease, Marfan's syndrome, osteogenesis imperfecta, neoplastic growth in collagenous tissue, dwarfism, rheumatoid arthritis, osteo-arthritis and vasculitis syndrome.

Three known classes of human collagen have been described to date. The Class I collagens, subdivided into type I, II, III, V, and XI are known to form fibrils. The amino-acid sequence of type I–III (to the extent it has been elucidated) is given in Appendix A of WO95/08115.

Collagen type I accounts for more than 90% of the organic matrix of bone. Therefore, in principle, it is possible to estimate the rate of bone resorption by monitoring the degradation of collagen type I. Likewise, a number of other disease states involving connective tissue can be monitored by determining the degradation of collagen. Examples are collagen type II degradation associated with rheumatoid arthritis and osteo-arthritis and collagen type III degradation in vasculitis syndrome.

Amino acid sequences of human type III collagen, human pro α1 (II) collagen, and the entire prepro α1 (III) chain of human type III collagen and corresponding cDNA clones have been investigated and determined by several groups of researchers; see Loil et al., Nucleic Acid Research 12:9383–9394 (1984): Sangiorgi et al., Nucleic Acids Research, 13:2207–2225 (1985); Baldwin et al., Biochem J., 262:521–528 (1989); and Ala-Kokko et al., Biochem. J., 260:509–516 (1989).

Type I, II and III collagens are all formed in the organism as procollagen molecules, comprising N-terminal and C-terminal propeptide sequences, which are attached to the core collagen molecules. After removal of the propeptides, which occurs naturally in vivo during collagen synthesis, the remaining core of the collagen molecule consists largely of a triple-helical domain having terminal telopeptide sequences (one N-terminal, one C-terminal) which are non-triple-helical. These telopeptide sequences have an important function as sites of intermolecular crosslinking of collagen fibrils extracellularly. The alphahelical region also includes crosslinkable sites.

Intermolecular cross-links provide collage fibrils with biomechanical stability. The formation of these cross-links is initiated by modification of lysine and hydroxylysine residues to the corresponding aldehydes. Several of these residues located on adjacent chains of collagen will spontaneously form different intermolecular cross-links. The exact position of the sites for cross-linking on collagen telopeptides and from the helical region has been previously described. See, for example, Kühn, K., in *Immunochemistry of the Extracellular Matrix*, Furthmayr, H., ed. 1:1–29 (1982). Two are aldehyde sites, one in each telopeptide region. The other two sites are hydroxylysine symmetrically placed at about 90 residues from each end of the molecule. When collagen molecules pack into fibrils, these latter sites in the helical region align and react with telopeptide aldehydes in adjacent molecules.

As illustrated by formula in EP-0394296 discussed below, the two 3-hydroxypyridinium cross-links have been found to be hydroxylysyl pyridinoline (also known as "pyridinoline") and lysyl pyridinoline (also known as "deoxypyridinoline"). These cross-linking compounds are naturally fluorescent. Some hydroxylysyl pyridinoline cross-links are found to be glycosylated as discussed for instance EP-A-0424428.

However, as described in Last et al., Int. J. Biochem. 22:559–564 (1990), other crosslinks occur naturally in collagen.

A number of known assays are directed at measuring the amount of 3-hydroxypyridinium or other crosslinks. See, for background and as examples, Wu and Eyre, Biochemistry, 23:1850 (1984); Black et al., Annals of the Rheumatic Diseases, 45:969–973 (1986); and Seibel et al., The Journal of Dermatology, 16:964 (1989). These reports describe hydrolyzing peptides from body fluids and then looking for the presence of free 3-hydroxypyridinium residues.

Assays for determination of the degradation of type I, II, and III collagen are disclosed in EP-0394296 and U.S. Pat. Nos. 4,973,666 and 5,140,103. However, these patents only describe non-isomerized collagen fragments containing the cross-linker 3-hydroxypyridinium. Furthermore, the above mentioned assays require tedious and complicated purifications from urine of collagen fragments containing 3-hydroxypyridinium to be used for the production of antibodies and for antigens in the assays.

At present very few clinical data using the approach described in U.S. Pat. Nos. 4,973,666 and 5,140,103 are available. Particularly, no data concerning the correlation between the urinary concentration (as determined by methods described in the above mentioned patents) of 3-hydroxypyridinium containing C-terminal telopeptides of type I collagen and the actual bone loss (as determined by repeated measurements by bone densitometry) have been published. The presence of 3-hydroxypyridinium containing telopeptides in urine requires the proper formation in bone tissue of this specific cross-linking structure at various times before the bone resorbing process. Very little information on these processes is available and it would be desirable to avoid this dependence of the correct formation of the cross-linking structure.

GB Patent Application No. 2205643 reports that the degradation of type III collagen in the body can be quantitatively determined by measuring the concentration of an N-terminal telopeptide from type III collagen in a body fluid. This method uses antibodies generated to N-terminal telopeptides released by bacterial collagenase degradation of type III collagen, said telopeptides being labelled and used in the assay.

The development of a monoclonal antibody raised against pepsin-solubilized type I collagen is described in Werkmeister et al., Eur. J. Biochem. 1987:439–443 (1990). The antibody is used for immunohistochemical staining of tissue segments and for measuring the collagen content in cell cultures. The measurements are not carried out on body fluids.

EP Patent Application No. 0505210 describes the development of antibody reagents by immunization with purified cross-linked C-terminal telopeptides from type I collagen. The immunogen is prepared by solubilizing human bone collagen with bacterial collagenase. The antibodies thus prepared are able to react with both cross-linked and non-cross-linked telopeptides, and with cross-linkers other than pyridinoline.

WO94/03813 describes a competitive immunoassay for detecting collagen or collagen fragments in a sample wherein a binding partner containing a synthetic linear peptide corresponding to the non-helical C-terminal or N-terminal domain of collagen is incubated with an antibody to the linear synthetic peptide and the sample, and wherein the binding of the antibody to the binding partner is determined.

WO95/08115 relates to assay methods in which collagen fragments in a body fluid are determined by reaction with an antibody which is reactive with a synthetic peptide. The assay may be a competition assay in which the sample and such a peptide compete for an antibody, possibly a polyclonal antibody raised against fragments of collagen obtained by collagenase degradation of collagen. Alternatively, it may be an assay in which an antibody, possibly a monoclonal antibody, is used which has been raised against such a synthetic peptide.

One peptide used in this disclosure is EKAHDGGR (SEQ ID NO:8). Generally, the peptides are chosen to include the cross-linking site K.

It was reported in Bonde et al., Journal of Bone and Mineral Research Vol. 10: S271—Abstract S481 (1995) that a polyclonal assay in which binding to antibodies is competed for between constituents of a sample and immobilized peptide of the sequence EKAHDGGR (SEQ ID NO:8) will respond to sample containing the hexapeptide AHDGGR (SEQ ID NO:9).

A poster exhibited by the authors at the ASBMR meeting in 1995 disclosed that this octapeptide was EKAHβDGGR (SEQ ID NO:3) (i.e., the isomerized form).

WO96/30765 reports that some "peptide" fragments in body fluid have amino acid sequences that differ from each other by virtue of the isomerization of aspartic acid to isoaspartic acid (alternatively referred to as β-aspartic acid). The term "peptide" is indicated here in quotes because such an isomerized aspartic acid residue does not form a peptide bond with the proximal C-terminal residue.

The isomerization has the effect of transferring that part of the peptide chain which runs downstreamn of the aspartic acid residue in the carboxyl terminus direction from the alpha carboxylic acid of the aspartic acid to which it is bonded via a peptide bond in the normal protein to the side chain carboxylic acid in a non-peptide amide bond, as shown below:

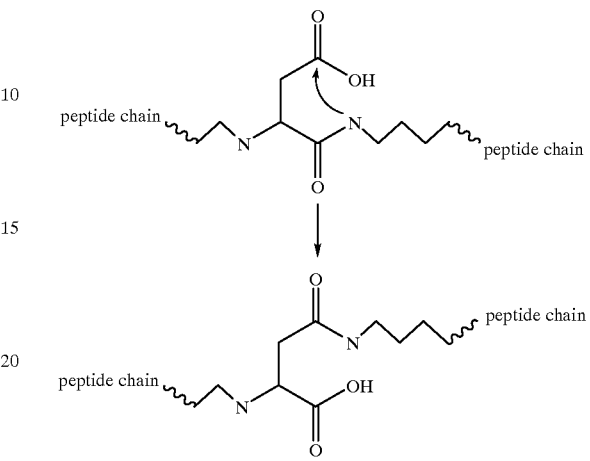

The isomerization of proteins containing aspartic acid has been reported previously to be a spontaneous reaction occurring under physiological conditions. See for instance Brennan et al., Protein Science 2: 331–338 (1993); Galletti et al., Biochem. J. 306: 313–325 (1995); Lowenson et al., Blood Cells 14: 103–117 (1988); and Oliya et al., Pharmaceutical Research, 11: 751 (1994).

Similar isomerization can occur in proteins containing asparagine residues (i.e., with —$NH_2$ instead of —OH in the starting protein in the above reaction scheme).

The references described above focus on, or in some cases are limited to, antibody detection of peptides that are cross-linked, or at least contain the cross-linking residue or the cross-linkable site. None of these references report the detection or the effective use of peptides having no cross-linkable site.

SUMMARY OF THE INVENTION

The present invention is based, in part on the surprising discovery that equally good or better results can be obtained in a competition assay in which the competition agent does not include the crosslinking lysine residue (K). In particular, an assay in which a peptide or isomerized peptide containing only the sequence AHDGGR (SEQ ID NO:2) from type I collagen, optionally with linking amino acids at its N-terminal end, provides surprisingly superior results in comparison with an assay based on the sequence EKAHDGGR (SEQ ID NO:1). In each instance D includes both aspartic acid and β-aspartic acid.

Accordingly, the present invention now provides a method of measurement of type I collagen degradation products in a body fluid comprising conducting a competition immunoassay in which sample molecules compete with a peptide or isomerized peptide in binding to an immunological binding partner for the peptide or isomerized peptide respectively, wherein the peptide or isomerized peptide comprises the amino acids AHDGGR (SEQ ID NO:2) optionally extended at the N-terminal end with one or more amino acids that do not form a contiguous sequence with AHDGGR (SEQ ID NO:2) in type I collagen, and wherein D represents aspartic acid or β-aspartic acid.

Said peptide or isomerized peptide may preferably be extended at the N-terminal end, e.g., with up to 10, more preferably up to 8, e.g., 3 to 6 amino acids, most preferably 4 amino acids.

Said 4 amino acids are preferably CGGG (SEQ ID NO:4) such that said peptide or isomerized peptide has the sequence CGGGAHDGGR (SEQ ID NO:5). Preferably, said additional amino acids serve to link the said peptide or isomerized peptide to a carrier molecule such as thyroglobulin or bovine serum albumin.

Said immunological binding partner may be present in a polyclonal antiserum or as a monoclonal antibody, e.g., a monoclonal antibody raised against an amino acid sequence comprising AHDGGR (SEQ ID NO:2), wherein D is aspartic acid or β-aspartic acid, optionally extended at the N-terminal end with further amino acids in the same manner as discussed above in relation to the peptide or isomerized peptide used in the assay.

Preferably, the monoclonal antibody has been raised against the amino acid sequence EKAHDGGR (SEQ ID NO:1), wherein D is as defined above.

BRIEF DESCRIPTION OF THE DRAWINGS

FIG. 1: Separation by HPLC of a synthetic peptide and a peptide analogue of the sequence EKAH*GGR (SEQ ID NO:1) differing at * between isoaspartic acid (peak 2) and normal aspartic acid (peak 3) as described in Example 3a.

FIG. 2: The differing reactivity of the separated peptide and peptide analogue of FIG. 1 in two forms of ELISA, as described in Example 3a.

DETAILED DESCRIPTION

Figure 1:
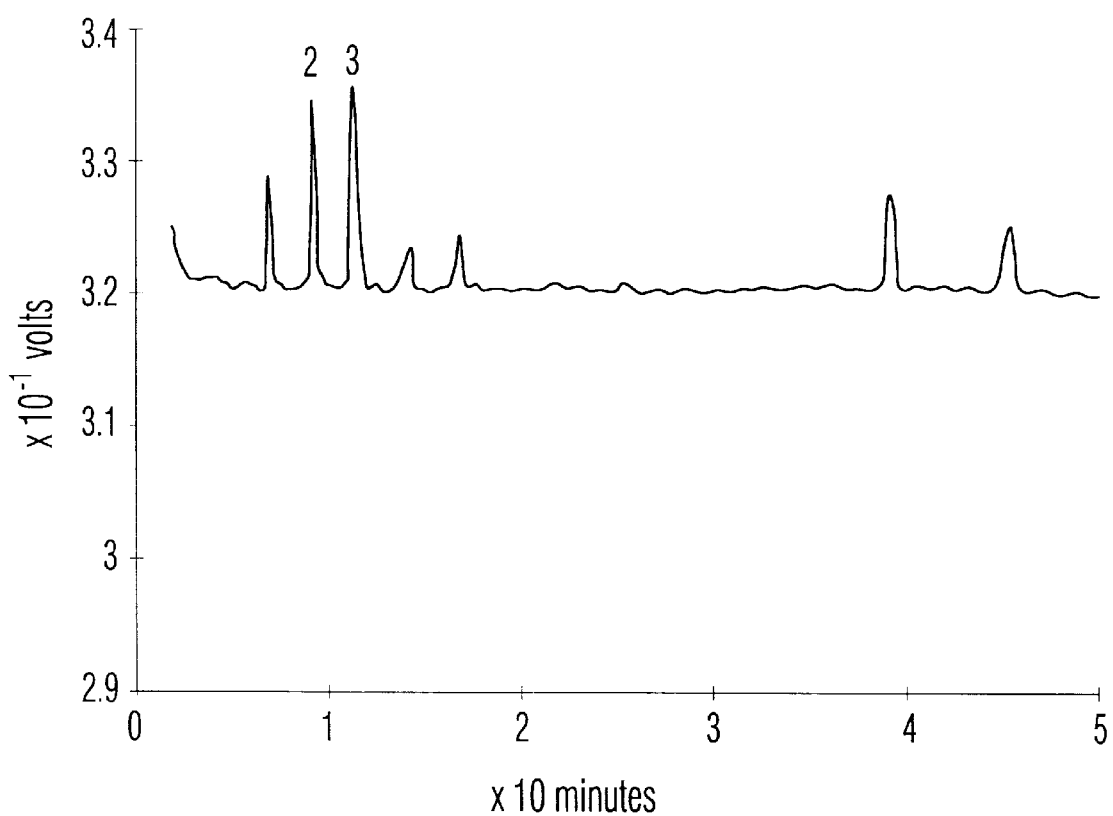

In a preferred embodiment of the method according to the invention, the assaying of type I collagen fragments, preferably in urine, or in another body fluid, including but not limited to serum or synovial fluid, is performed by an inhibition ELISA (enzyme linked immunosorbent assay) by metering off a sample of body fluid and contacting the sample with the synthetic isomerized peptide CGGGAHβDGGR (SEQ ID NO:10) and with an antibody which is immunoreactive with the synthetic isomerized peptide. The synthetic isomerized peptide is immobilized on a solid support. The antibody is raised against the synthetic isomerized peptide containing the sequence AHβDGGR (SEQ ID NO:11). Alternatively, the antibodies may be raised against collagenase treated collagen (CTC).

The combined reagents and sample are incubated, and a peroxidase-conjugated (revealing) antibody is added. After another incubation, a peroxidase substrate solution is added. Following short final incubation, the enzyme reaction is stopped, and the absorbance is measured at 450 nm and compared with a standard curve obtained with standard solutions by the same procedure.

Synthetic isomerized peptides are used for the preparation of standards. The concentration of synthetic isomerized peptide in a stock solution is determined by quantitative amino acid determination. A two-fold dilution of the stock solution is prepared and subsequently used for the construction of the standard curve in the inhibition ELISA.

Preparation of Synthetic Isomerized Peptides

The preparation of synthetic peptides may be performed according to procedures well known in the art, e.g., by solid-phase peptide synthesis techniques commonly described as "Merrifield synthesis". Also classical solution phase techniques may be used. Sequences of interest include potential sites for crosslinking (see, for example, Kühn, K., in *Immunochemistry of the Extracellular Matrix* 1:1–29 (1982), Eyre, D. R., Ann. Rev. Biochem. 53:717–48 (1984), or U.S. Pat. No. 5,140,103).

Regarding the synthetic isomerized peptides, it is possible to omit (or add) one or more amino acid residues from (or to) the N-terminus sequences without substantial loss of the ability to (a) raise antibodies recognizing the corresponding native collagen fragment or (b) inhibit the bindings of such antibodies to the native fragment. It is possible to use longer collagen fragments and/or chimeric peptides to raise the antibodies and, in principle, it is not necessary to use the same isomerized peptide as the immunogen and the competitor in the assay.

Preparation of Antibodies

The methods of preparation of both monoclonal and polyclonal antibodies are well known in the art. For example, see Campbell, A. M., *Laboratory Techniques in Biochemistry and Molecular Biology*, Vol. 13 (1986). It is possible to produce antibodies to synthetic isomerized peptides by immunization. However, because of the relatively small molecular weight of these compounds it is preferred that the hapten be conjugated to a carrier molecule. Suitable carrier molecules include, but are not limited to, bovine serum albumin, thyroglobulin, ovalbumin, tetanus toxoid, and keyhole limpet hemocyanin. The preferred carrier is thyroglobulin. To present the hapten in its most immunogenic form to the antibody producing cells of the immunized animal a number of alternative coupling protocols can be used. Suitable procedures include, but are not limited to, glutaraldehyde, carbodiimide, and periodate. The preferred binding agent, however, is maleimide by which a cysteine terminated peptide may be conjugated specifically via the cysteine amino acid.

Alternatively, the antibodies can be raised against collagenase treated collagen (CTC). For example, human bone collagen may be obtained by removing the femur of a 2–3 day old cadaver and cleaning off all soft tissue. The femur is then divided into 2–3 cm slices. The slices are washed with distilled water for one hour, defatted with acetone for three hours, and then washed again twice for one hour with distilled water. The slices are then frozen at −20° C., lyophilized for five days, and then ground finely.

100 gm of dried bone powder is suspended in 500 ml of 5M guanidinehydrochloride for two hours and then washed five times in distilled water. The bone powder is extracted twice for 24 hours with 500 ml of 0.5M EDTA, pH 7.5, containing protease inhibitors (for example, 5 mM benzamidine, 50 μM phenylmethylsulfylfluoride, hudroxymercuribenzoic acid, and 0.6 MIU aprotini). The demineralized bone powder is washed extensively on a Buchner funnel.

50 gm of demineralized bone powder is solubilized in 0.05 M Tris containing 36 mM $CaCl_2$, pH 7.5, up to 150 ml. 1 gm of bacterial collagenase 1A (Sigma, St. Louis, Mo., Cat. No. C.9891) is added and the mixture is incubated for 18 hours at 37° C. in a water bath. The mixture is stirred during the incubation. Following the incubation, the supernatant is collected, dried under vacuum, and stored at —20° C.

Figure 3A:
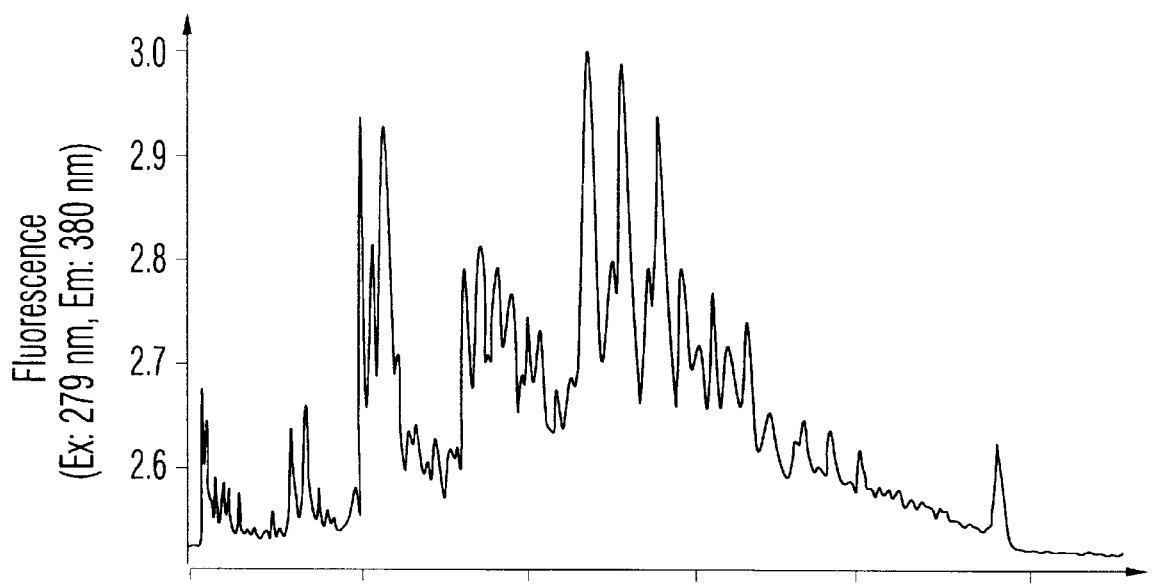
FIGS. 3(a) and (b): Fluorescence (a) and absorbance (b) of cross-linked peptides and peptide analogues from urine separated by HPLC as described in Example 3(b).
Figure 3B:
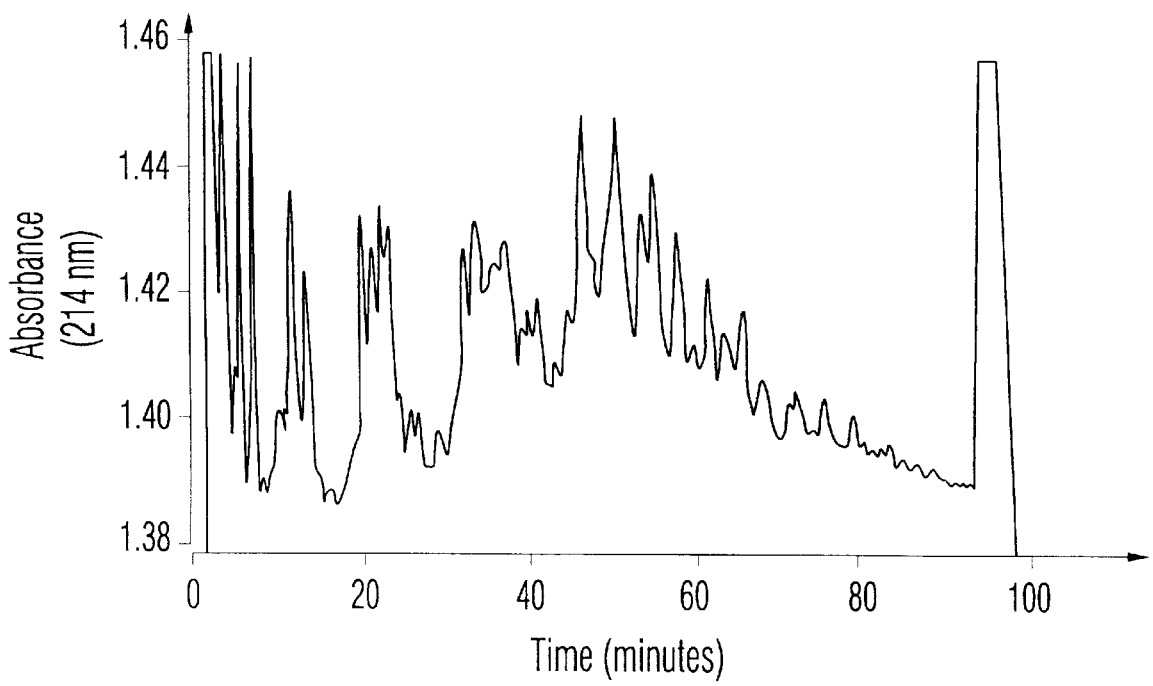

The dried material is resuspended in 20 ml 10% (v/v) acetic acid. Insoluble material is removed by centrifugation at 2000×g for 10 min. The supernatant is applied to a column (dimensions 2.4×90 cm) of PD-10 (BioRad, Hercules, Calif.) equilibrated with 10% acetic acid. The chromatographic separation is performed at a flow rate of 12 ml/hour and approximately 100 fractions of 6 ml each are collected. Fractions are measured in the CrossLaps™ ELISA (Osteometer BioTech A/S, Denmark), and samples containing at least 10% of the peak fraction activity are pooled. The pool is dried under vacuum. Alternatively, the collagen fragments separated by the column can be assayed by measuring protein absorbence at 280 nm and the fluorescence of pyridinoline cross-linked peptides, as described in Example 3(b), below (see FIGS. 3a and 3b). The first of two fluorescent peaks is enriched for fragments containing the C-terminal telopeptide region (see Hanson et al., 1992, J. Bone & Min. Res. 7: 1251–1258).

The dried collagen fragments are resuspended and conjugated to a suitable carrier protein (e.g., BSA) and used to raise antibodies according to routine methods known in the art, as detailed below.

The preparation of antibodies is carried out by conventional techniques including immunization with collagen fragments or synthetic peptides conjugated to a carrier. To improve the immunogenicity it is preferred that the immunogen be mixed with an adjuvant before injection. Examples of adjuvants include, but are not limited to, aluminum hydroxide, Freund's adjuvant, and immune-stimulating complexes (ISCOMs). ISCOMs can be made according to the method described by Morein, B. et al., *Nature* 308:457–460 (1984).

Either monoclonal or polyclonal antibodies to the hapten carrier molecule can be produced. For the production of monoclonal antibodies it is preferred that mice are immunized. Spleen cells from the immunized mouse are harvested, homogenized, and thereafter fused with cancer cells in the presence of polyethylene glycol to produce a cell hybrid which produces monoclonal antibodies specific for isomerized peptide fragments derived from collagen. Suitable cancer cells include, but are not limited to, myeloma, hepatoma, carcinoma, and sarcoma cells. Detailed descriptions of the production of monoclonal antibodies are provided in Goding, J. W., in *Monoclonal Antibodies: Principles and Practice*, (1986). A preferred preliminary screening protocol comprises the use of synthetic isomerized peptides conjugated to a carrier and coated on to the solid surface of a microtitre plate.

For the preparation of polyclonal antibodies, which are reactive with isomerized peptide fragments derived from collagen, different animal species can be immunized. Suitable species include, but are not limited to, chicken, rabbit and goat. Chicken and rabbit are preferred.

Antibody fragments are prepared by methods known in the art (see E. Ishikawa, J. of Immunoassay 3: 209–327 (1983)).

Conduct of Immunoassays

By utilization of an immunoassay with the antibodies prepared as above it is possible to assay a biological sample of body fluid, including but not limited to urine, serum, or synovial fluid, without prior fractionation or hydrolysis. The specificity for the desired collagen in the biological fluid is supplied by the antibody in combination with the use of a synthetic isomerized peptide (against which the antibody was raised or in any event with which the antibody is immunochemically reactive) in the assay construction.

The immunoassays are conducted using any procedure selected from the variety of standard competition assay protocols generally known in the art. As it is generally understood, the assay is constructed so as to rely on the interaction of the specific immunological binding partner with collagen fragments in the sample and to utilize some means to detect the complex formed by the analyte and the immunological binding partner. The peptide or isomerized peptide may be complexed to a solid support and used as a capture immunological binding partner for the collagen fragments. The specific design of the immunoassay protocol is open to a wide variety of choice, and the number of clinical assay devices and protocols available in the art is multitudinous. For a variety of such protocols, see U.S. Pat. No. 5,001,225.

A homogeneous assay format may be used in which for instance latex particles are conjugated to the peptide or isomerized peptide and the sample and the particles compete to bind the antibody. Specific agglutination of the particles by antibody produces a change which is optically detectable as a change in scattering or absorbance and which is inhibited by crosslinks in the sample.

The antibodies and revealing reagents for the conduct of an immunoassay using standard detection protocols, for example radioisotope labelling, fluorescent labelling or ELISA, may conveniently be supplied as kits which include the necessary components and instructions for the assay. In one embodiment of the invention such a kit includes a microtitre plate coated with a relevant synthetic isomerized peptide, standard solutions for preparation of standard curve, a urine control for quality testing of the analytical run, rabbit antibodies reactive with the above-mentioned synthetic isomerized peptide, anti-rabbit immunoglobulins conjugated to peroxidase, a substrate solution, a stopping solution, a washing buffer and an instruction manual.

Since immunoassays can be constructed using antibodies and specific synthetic peptides or isomerized peptides, the ratios of the corresponding collagen fragment sequences in an appropriate biological fluid can be determined as well as their individual levels and their total. Thus, the assay can be designed to include antibodies which will result in determination of a single peptide sequence, or any desired combination thereof.

In addition to the detection of peptide fragments in assays using the peptides or isomerized peptides specified herein, bone metabolic balance is advantageously determined by the substantially simultaneous determination of a marker of the formation of bone in the same or other appropriate biological fluid from the same individual. "Substantially simultaneous" means the same day, preferably within 4 hours. For example, such markers include osteocalcin (also known as bone GLA protein or BGP) procollagen type I, bone alkaline phosphatase, and total alkaline phosphatase. Suitable methods for the determination of these markers can be found, for example, in Delmas, P. D., et al., J. Bone Min. Res. 1:333–337 (1986).

The assay of the present invention which provides an index for determination of the metabolic status of tissues, which generate collagen-derived peptides or isomerized peptides when degradation occurs, are useful in a variety of contexts. First, when considering the degradation of type I collagen, the assays are methods to assess an abnormal condition of a subject by indicating, for example, excessive bone resorption. The assays, therefore, are used to diagnose and monitor an osteoporotic condition or the metastatic progress of a malignancy. Other conditions characterized by excessive bone resorption, which can also be diagnosed or monitored using the assays described herein, include Paget's disease and hyperparathyroidism. Since the condition of the subject can be monitored continuously, application of these assays can also be used to monitor the progress of therapy administered to treat these or other conditions. Further, the assays can be used as a measure of toxicity, since the administration of toxic substances often results in tissue degradation.

Thus, the assays may be applied in any situation wherein the metabolic condition of collagen tissues can be used as an index of the condition, treatment, or effect of substances directly administered to the subject or to which the subject is exposed in the environment.

The invention is illustrated by the following examples.

EXAMPLE 1

IMMUNOASSAYS FOR SPECIFIC PEPTIDE SEQUENCES IN URINE

The following three isomerized peptides, designated $\alpha 1(I)$ C1, $\alpha 1(I)$N1, and $\alpha 2(I)$ N1, each having cross-linkable sites, were prepared by solid-phase techniques are used for the preparation of immunogens.

1. $\alpha 1(I)$N1: (Iso)Asp-Glu-Lys-Ser-Thr-Gly-Gly (SEQ ID NO:6)
2. $\alpha 1(I)$C1: Glu-Lys-Ala-His-(Iso)Asp-Gly-Gly-Arg (SEQ ID NO:3)
3. $\alpha 2(I)$N1: Gln-Tyr-(Iso)Asp-Gly-Lys-Gly-Val-Gly (SEQ ID NO:7)

For immunization, the peptide isomers are covalently attached to bovine serum albumin using carbodiimide or glutaraldehyde reagents and methods well known in the art. Both monoclonal and polyclonal antibodies are raised against the peptide isomers. For production of monoclonal antibodies, Balb/c mice are immunized with peptide isomer-BSA conjugates, and hybridoma cell lines are prepared using standard techniques after fusion of cells from the spleen or lymph nodes with Ag8 myeloma cells. Polyclonal antibodies are raised in rabbits and chicken. Screening of both antisera and hybridoma cell media were performed by ELISA using microtitre plates coated with the appropriate peptide isomer-protein carrier conjugate prepared using carbodiimide reagents and methods well known in the art.

Assays for three of the peptide isomer sequences ($\alpha 1(I)$ C1, $\alpha 1(I)$N1, and $\alpha 2(I)$N1) in urine are performed by an inhibition ELISA as follows:

Urine samples (10 to 25 µl) possibly containing collagen fragments or solutions containing 0.015–15 µg peptide isomer/ml as reference standards, respectively, are added to 75 µl of immunological binding partners for the peptide isomers diluted 1:5,000–1:20,000 in phosphate buffered saline containing 0.1% Tween-20 detergent (PSB-T) and including 0.1% (w/v) of BSA. Each sample is prepared in duplicate in flat-bottomed, 96-well microtitre plates previously coated with peptide isomer-protein carrier conjugate containing the appropriate peptide isomer. After 60 minutes, the plates are washed with PBS-T (3 times) and the bound antibodies are detected by standard techniques with a horseradish peroxidase labelled antibody prepared against the species of the primary antibody. Peroxidase substrate is added and the color development is measured at 450 nm in an automated microtitre plate reader after stopping the enzyme reaction using 1 M $H_3PO_4$. Samples containing the analyte decrease the binding of primary antibody to the immobilized peptide isomer on the plate and thus have a reduced color concentration. The amount of analyte in the sample is quantified with reference to previously established curves from standards included on each plate computed using loglin plots.

EXAMPLE 2

ASSAY USING A MONOCLONAL ANTIBODY FOR DETECTION OF DEGRADATION PRODUCTS OF TYPE I COLLAGEN

Monoclonal antibodies were developed by immunization of mice with isoaspartic acid containing $\alpha 1(I)C1$ synthetic peptide analogue conjugated to an appropriate carrier protein. Cell fusion, cloning and propagation of hybridomas were performed according to standard procedures. Screening procedures included testing of reactivity to $\alpha 1(I)C1$ synthetic peptide analogue immobilized on microtitre plates.

The specificity of the antibodies was tested by inhibition studies using different overlapping sequences from the C-telopeptide of type I collagen in peptide analogue form, i.e., including the isomerized linkage as aspartic acid.

An assay using one such antibody MAbA-ISO is developed. In brief, the isoaspartic acid containing synthetic peptide analogue $\alpha 1(I)C1$ is conjugated to bovine serum albumin using carbodiimide or glutaraldehyde, and the conjugate is used for coating of microtitre plates. Alternative material can also be used, the essential feature being exposure of the sequence EKAHiDGGR (SER ID NO:3).

Following coating, the wells of the microtitre plates are incubated with 15 µl of urine and 100 µl of MAbA-ISO conjugated to horseradish peroxidase.

After one hour the plates are washed and substrate (e.g., TMB) is added.

EXAMPLE 3

CORRELATION OF ELISA FOR ISOASPARTIC ACID PEPTIDE ANALOGUE TO ELISA ASSAYS BASED ON OTHER PEPTIDE FRAGMENTS AND ANTIBODIES

The correlation between a polyclonal ELISA according to this invention and an MAbA7 ELISA as described in WO95/08115 on HPLC separated peptide species, (a) synthetic and (b) isolated from urine, was evaluated. The MAbA7 ELISA is a competitive assay wherein the MAbA7 monoclonal raised against the 8AA peptide (EKAHDGGR (SEQ ID NO:8) in which D is normal aspartic acid) is used and collagen degraded collagen immobilized in a microtitre tray competes with collagen fragments in the sample for binding to the monoclonal antibody (MAbA7).

The ELISAs used in this example are carried out as follows:

(A) THE POLYCLONAL ISO-ELISA

The polyclonal ELISA is based on an immobilized synthetic peptide analogue with an amino acid sequence of eight amino acids (8AA) specific for an isomerized part of the C-telopeptide of the al-chain of type I collagen (Glu-Lys- Ala-His-(Iso)Asp-Gly-Gly-Arg; SEQ ID NO:3). During incubation with an antibody reactive with this sequence, a competition takes place between the immobilized peptide iso-form analogue and the breakdown products of the α1-chain of type I collagen in the sample.

Briefly, a 25 μL sample or standard is added to each well of a 8AA antigen-coated microplate, followed by 75 μL of antiserum raised against collagenase treated type 1 collagen. The plates are incubated for 1 hour at room temperature under agitation and washed five times with a washing buffer. A goat anti-rabbit immunoglobulin G horseradish peroxidase conjugate (100 μL) is added to each well. After incubation for 1 hour at room temperature, plates are washed five times as before. The enzyme substrate (100 μL/well) is added, and after 15 minutes of incubation in the dark, the reaction is stopped by adding 100 μL phosphoric acid (1 mol/L). The optical density of 450 nm is measured with a microplate reader. Duplicate measurements are performed for each sample, and the data are expressed as nanograms per mol creatinine (Cr), measured by a standard colorimetric technique. This assay is referred to herein as ISO-ELISA.

(B) THE MAbA7 ELISA

MAbA7 is a monoclonal antibody raised as described above in mouse against the peptide of the sequence EKAHDGGR (SEQ ID NO:8), i.e., with normal aspartic acid.

This assay version is carried out in three steps as follows:

In the first step the wells of a microtitre plate pre-coated with purified collagenase-treated collagen (CTC) are incubated for 1 hour at room temperature with 15 μl standard solution or sample and 100 μl of peroxidase-conjugated monoclonal antibody solution.

After washing in the second step the wells are incubated in the dark for 15 minutes at room temperature with 100 μl substrate solution. Finally, in the third step, the color reaction is stopped by the addition of 100 μl stopping solution. The absorbance at 450 nm is measured within 2 hours.

EXAMPLE 3(a)

This example demonstrates that antibodies specific for either synthetic EKAHDGGR (SEQ ID NO:8) or EKAHiDGGR (SEQ ID NO:3) can be developed.

A mixture of synthetic EKAHDGGR (SEQ ID NO:8) and EKAHiDGGR (SEQ ID NO:3) was separated by HPLC (FIG. 1, peak 3 and peak 2, respectively). Sequence analysis confirmed that peak 2 contained isomerized aspartate. This was indicated by the sequencing operation being halted after the histidine residue. Peak 3 contained regular aspartate and sequencing was able to proceed normally. Fractions from the HPLC profile were collected and tested for immunoreactivity in both MAbA7 ELISA and polyclonal ISO-ELISA. It was demonstrated that the two assays detected separate peaks, i.e., peak 2 was detected by ISO-ELISA and peak 3 by MAbA7 ELISA.

Figure 2:
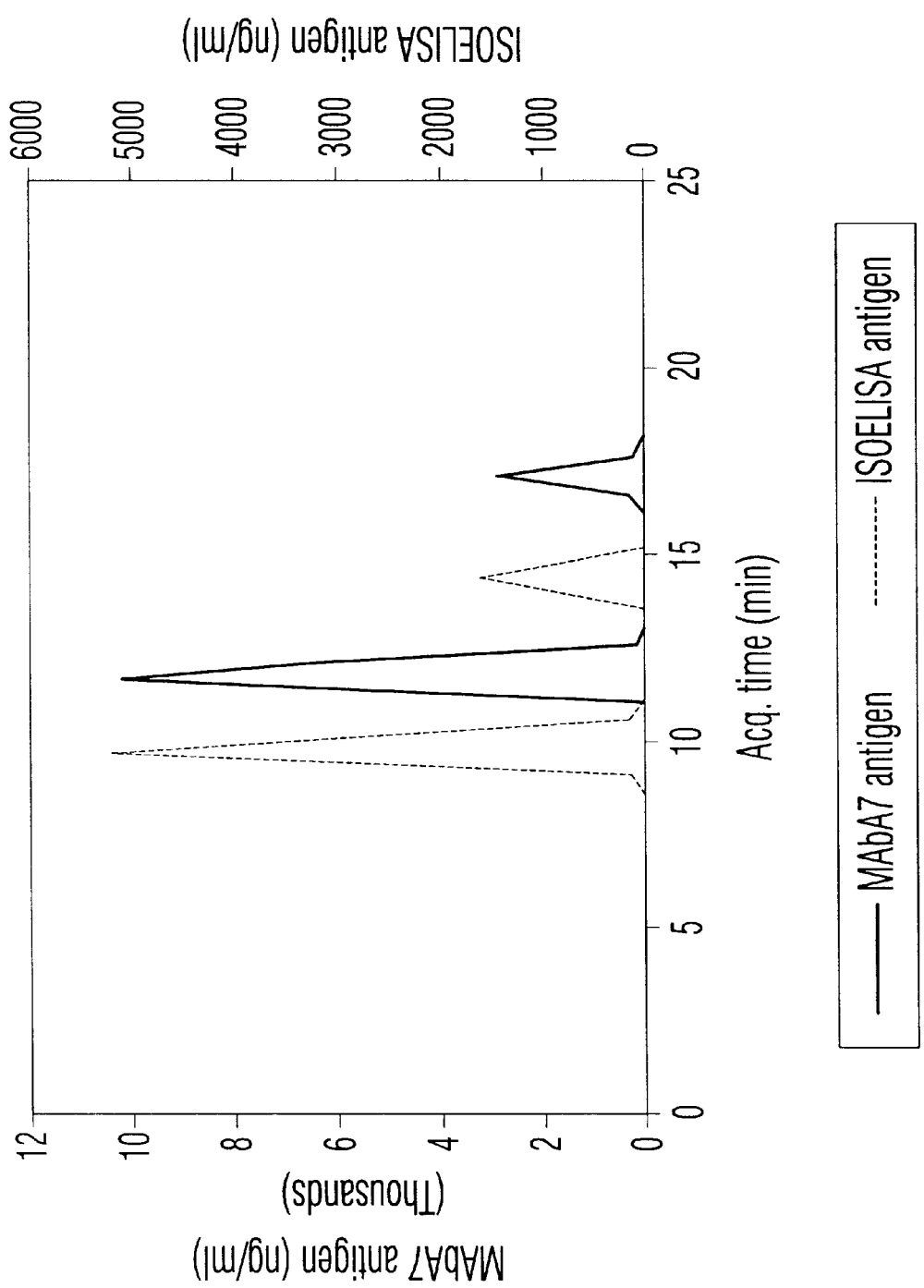

The results are shown in FIG. 2.

EXAMPLE 3(b)

This example demonstrates that ISO-ELISA-related molecules can be purified from urine, and that these molecules can be separated into di-peptide related species containing isomerized or regular aspartate.

First urine was immunopurified using MAbA7. MAbA7 was coupled to CNBr activated Sepharose™ according to the manufacturer's instructions. Urine was diluted 1:3(v/v) in PBS buffer and the pH adjusted to 8.0 using 1 M NaOH. Eight hundred ml diluted urine was recirculated on to a column (14 cm$^3$) for 24 hr at 4° C. at a flow rate of 0.8 ml/min. After washing the column with 200 ml PBS buffer, pH 8.0, bound antigens were eluted using 20 ml 50% saturated $(NH_4)_2SO_4$ containing 1% TFA (v/v) and stored at −20° C. The eluted antigens were desalted using a 1 ml C18 Sep-Pak™ column. The Sep-Pak™ column was conditioned with 20 ml 80% methanol (v/v) and equilibrated with 20 ml water containing 1% TFA (v/v) before adding the antigen. Bound antigens were washed with 20 ml of water containing 1% TFA (v/v) and eluted with 40% acetonitrile (v/v) containing 0.1% TFA (v/v), freeze-dried and stored at −20° C.

Molecules from selected peaks obtained by the above procedure were further separated by HPLC using trifluoroacetic acid (TFA) as ion pair. Fractions were analyzed by amino acid composition, amino acid sequencing, mass spectrometry, and immunoreactivity in MAbA7 and ISO-ELISA.

The fluorescence (3-hydroxypyridinium cross-links) and absorbance of the HFBA HPLC profile is demonstrated in FIG. 3. By further separation pure preparations were obtained and tested by mass spectrometry and immunoreactivity (Table 2), as well as amino acid sequencing (Table 3) and amino acid composition (Table 4). Data demonstrates that three separate molecules all with the molecular weight around 2036 Daltons could be identified (Table 2). Amino acid sequencing was blocked after histidine in peak F-24-17-10, whereas the complete sequence EKAHDGGR (SEQ ID NO:8) was obtained for the two other peaks (F-26-18-09 and F-29-19-24, Table 3). Amino acid composition analysis (which does not separate isomerized and regular aspartate) confirmed the three peaks contained the same amino acids.

These data suggest that three different, cross-linked dipeptide related species were identified in urine. The molecules differed in having either isomerized or regular aspartate in the sequence EKAHDGGR (SEQ ID NO:1). Peak F-24-17-10 is suggested to contain two peptide analogues of the sequence EKAHiDGGR (SEQ ID NO:3), peak F-26-18-09 one EKAHiDGGR (SEQ ID NO:3) and one EKAHDGGR (SEQ ID NO:8), and peak F-29-19-24 two cross-linked peptides of the sequence EKAHDGGR (SEQ ID NO:8).

Additionally, a similar observation was done on molecules of molecule weight around 2039. These did not contain 3hydroxypyridinium cross-links (as fluorescence was absent), and the nature of the cross-linker was not determined.

TABLE 2

Detection by MAbA7 and ISO-ELISA of Peptide related species separated by HPLC from Urine

| Fraction No. | Mass | Pyr | DPyr | MAbA7 ng/ml | ISO-ELISA ng/ml |
|---|---|---|---|---|---|
| F-18-17-14 | 2038.2 | | | 58 | 974 |
| F-20-18-18 | 2039.5 | | | 406 | 350 |
| F-22-18,19,20-16 | 2038.9 | | | 972 | 118 |
| F-24-17-10 | 2036.1 | + | | 114 | 2110 |
| F-26-18-09 | 2036.2 | + | | 2114 | 2203 |
| F-26-18-12 | 1858.9 | | + | 85 | 783 |
| F-29-19-24 | 2036.0 | + | | 3149 | 221 |
| F-30-20-12 | 1858.8 | | + | 2108 | 33 |

TABLE 3

Sequence Data for Peptide related molecules in
F-24-17-10, F-26-18-09, and F-29-19-24

| Cycle | F-24-17-10 | F-26-18-09 | F-29-19-24 | Expected |
|---|---|---|---|---|
| 1 | Glu | Glu | Glu | Glu |
| 2 | — | — | — | — |
| 3 | Ala | Ala | Ala | Ala |
| 4 | His | His | His | His |
| 5 | — | Asp | Asp | Asp |
| 6 | — | Gly | Gly | Gly |
| 7 | — | Gly | Gly | Gly |
| 8 | — | Arg | Arg | Arg |
| 9 | — | — | — | — |
| 10 | — | — | — | — |

TABLE 4

Amino Acid Composition of the Peptides
F-24-17-10, F-26-18-09, and F-29-19-24 (residue/peptide)

| Amino Acid | F-24-17-10 | F-26-18-09 | F-29-19-24 | Expected |
|---|---|---|---|---|
| Asp | 1.0 | 1.0 | 0.9 | 1 |
| Glu | 1.3 | 1.2 | 1.3 | — |
| Ser | 0.4 | 0.2 | 0.6 | — |
| Gly | 2.2 | 2.0 | 2.4 | 2 |
| His | 1.4 | 1.0 | 1.0 | 1 |
| Thr | 0.1 | 0.0 | 0.2 | — |
| Ala | 1.0 | 1.0 | 1.0 | 1 |
| Pro | 0.0 | 0.0 | 0.0 | — |
| Tyr | 0.0 | 0.0 | 0.0 | — |
| Val | 0.1 | 0.1 | 0.1 | — |
| Met | 0.0 | 0.0 | 0.0 | — |
| Ile | 0.1 | 0.1 | 0.1 | — |
| Leu | 0.1 | 0.1 | 0.2 | — |
| Lys | 0.3 | 0.1 | 0.3 | — |
| Arg | 0.8 | 0.9 | 0.8 | 1 |
| Total | 8.8 | 7.6 | 9.0 | 7 |

The polyclonal assay is shown to be specific for the peptide analogue containing isoaspartic acid residues and the MAbA7 assay is specific for the peptide containing normal aspartic acid residues. Di-peptide analogues containing both the isomerized as well as the non-isomerized aspartic acid will be detected by both assays.

The application of these two assays to a urine sample therefore allows a comparison to be made of the level of isoaspartic acid containing isomerized peptide and the level of the normal form, giving an indication of the degree to which old established bone tissue is being broken down.

EXAMPLE 4

The clinical significance of the presence of isomerized peptide analogues in serum was investigated by subjecting serum samples from postmenopausal women taken before and after treatment with a bisphosphonate, Ibandronate (Boehringer Mannheim), to analysis in both a serum version of the ISO-ELISA polyclonal assay described above and the MabA7 based ELISA monoclonal assay.

The assay developed for measurement of type I degradation products in serum is based on an immobilized synthetic peptide/peptide isomer mixture with the amino acid sequence EKAHDGGR (SEQ ID NO:1) present in peptide and in peptide isomer form. Rabbits were immunized with the isomerized peptide conjugated to BSA using a two step carbodiimide procedure. If the isomerized peptide is substantially more antigenic in the rabbits employed than the peptide form of the amino acid sequence one can immunize with the peptide/peptide isomer mixture conjugated to BSA. For coating of microtitre plates the peptide was conjugated to thyroglobulin using glutaraldehyde. During incubation with this antibody a competition takes place between the immobilized peptide isomer (the immobilized peptide being inactive in the assay) and the breakdown products of type I collagen in serum. As the content of the peptide in the solution increases, less antibody will bind to the immobilized peptide isomer leading to a decreasing optical density.

In brief, 50 $\mu$l Standard (synthetic 8AA-peptide isomer/peptide mixture) or unknown sample in a test tube is added 100 $\mu$l Assay Buffer (500 mM TRIS, 0.0% Tween 20, 1.0% BSA; pH=6.5). From these 150 $\mu$l, 50 $\mu$l is pipetted into the appropriate wells in the precoated ELISA plate. Then 50 $\mu$l Antibody Solution (rabbit antiserum to EKAHiDGGR (SEQ ID NO:3) diluted 1+20,000 in Assay Buffer) is added to each well, the plate is covered with sealing tape and incubated at room temperature for 60 min on a shaking device. All the following procedures were also carried out at room temperature. After incubation the plates were washed three times with diluted Washing Buffer (25 mmol/l TRIS and 50 mmol/l NaCl PH=7.2).

Peroxidase conjugated Antibody (HRP-conjugated goat antibodies to rabbit IgG (Jackson Immunochemicals, PA) diluted 1+4000 in Assay Buffer), 100 $\mu$l/well) was added and the sealed wells were incubated 60 min. on a shaking device. Following another washing procedure, 100 $\mu$l of TMB Substrate Solution was added to all wells which were sealed and incubated for 15 min. The enzyme reaction was stopped after 15 min by addition of 100 $\mu$l Stopping Solution. The optical density was read in an ELISA-reader at 450 nm.

A calibration curve was constructed on a log-linear graph paper by plotting the mean absorbances of the five standards (25 ng/ml–500 ng/ml). The concentration of EKAHiDGGR (SEQ ID NO:3) equivalent in each patient specimen were determined by interpolation on the calibration curve.

Figures 4, 5:
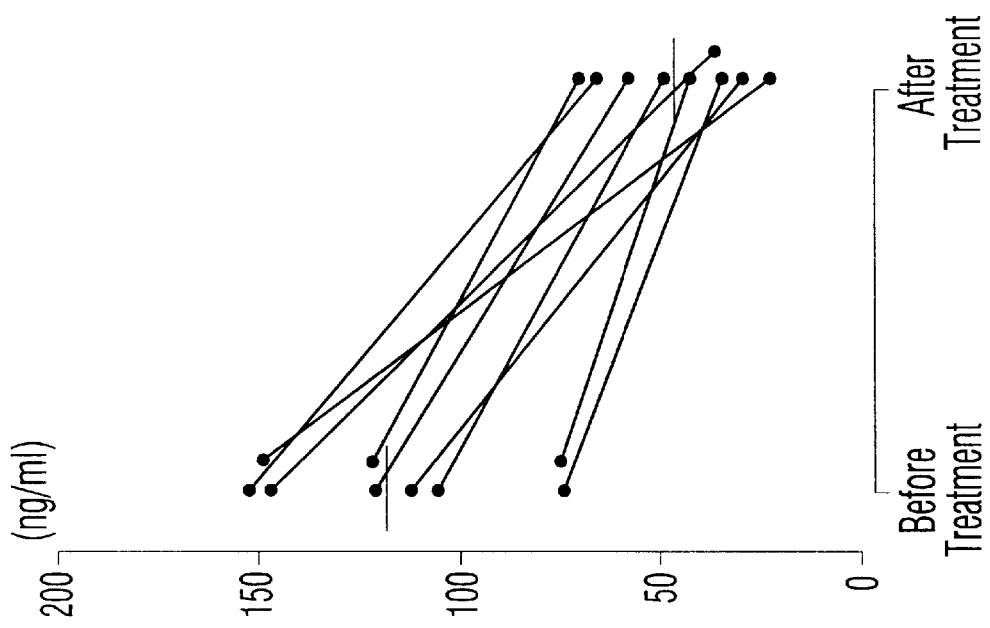
FIG. 4: Results of monitoring the effect of bisphosphonate treatment on bone resorption using the MAbA7 based ELISA as described in Example 4.
FIG. 5: Results of monitoring the effect of bisphosphonate treatment on bone resorption using the ISO-ELISA as described in Example 4.
Figure 6:
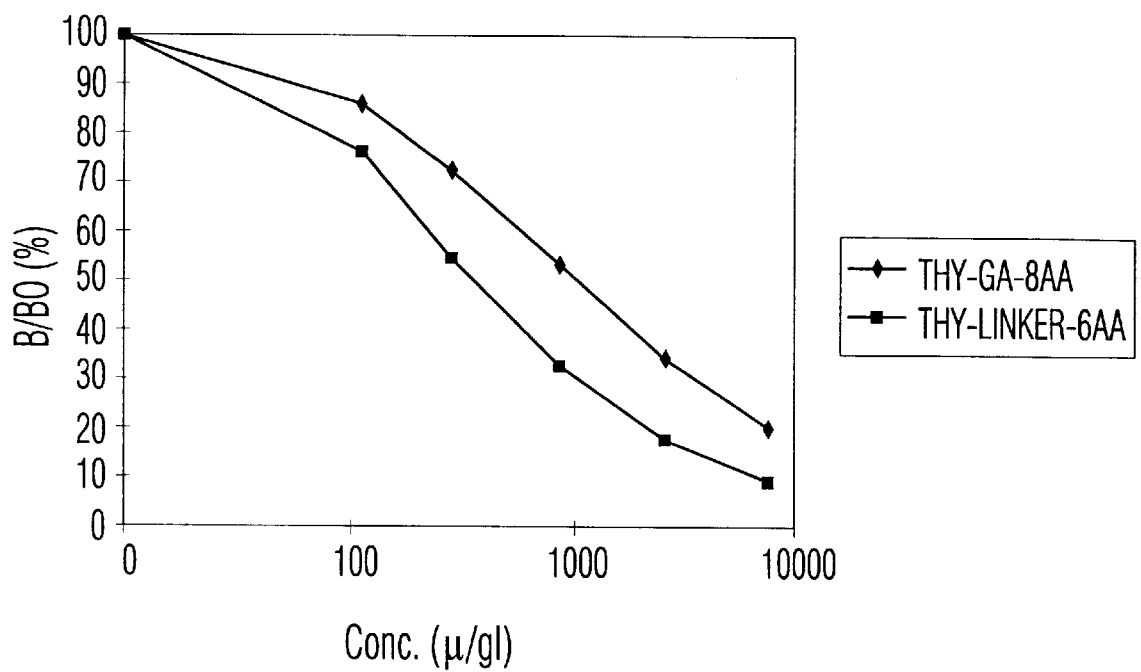
FIG. 6: Calibration curves obtained in Example 5 using the two different coating conjugates, 6AA and 8AA. Relative absorbance is plotted against concentration of antigen standard.

The results are shown in FIGS. 4 and 5. In FIG. 4, no significant change is seen in the serum level of molecules reactive in the monoclonal assay directed to molecules competing for antibody reactive with the peptide sequence EKAHDGGR (SEQ ID NO:8) before and after fifteen months treatment with a therapeutic expected to reduce the rate of bone resorption. In FIG. 5, one sees a drop of more than 60% following treatment for six months with 2.5 mg/day of Ibandronate in the level of molecules reactive in the polyclonal assay directed to molecules competing with the non-peptide EKAHiDGGR (SEQ ID NO:3) for antibody in the polyclonal serum, reflecting the expected result of the therapeutic treatment.

This example indicates that the sum of peptides in serum incorporating the sequence EKAHDGGR (SEQ ID NO:8), which may include cross-linked peptides of the kind described in U.S. Pat. No. 5,455,179 and similar molecules based on other cross-links or not cross-linked at all, are not indicators of the rate of bone resorption, but that the related non-peptide molecules produced by isomerization of the bonding of the aspartic acid in the amino acid sequence are.

It is suggested that the specificity for the isomerized analogue of the octapeptide leaves the ISO-ELISA insensitive to molecules present in serum which are reactive in the MabA7 ELISA. The level of isomerization is believed to be related to the age of the bone, being therefore a quantifiable marker for turnover of mature bone, whilst the molecules interfering in the monoclonal assay do not relate to bone resorption and could originate from the turnover of "young" collagen molecules, e.g., from proteolytic breakdown of extracellular collagen not yet incorporated into the bone matrix, or generated during turnover of short-lived type I collagen at non-skeletal sites.

Furthermore, although it is believed that the body has mechanisms for repairing damage to proteins by isomerization at aspartate, it may be that in bone collagen is shielded from these repair mechanisms making isomerization an unusually good indicator of the resorption of "old" collagen in the case of bone.

EXAMPLE 5

Conjugation of cys-gly-gly-gly-ala-his-βasp-gly-glY-arg (SEQ ID NO:10) to Thyroglobulin The isomerized peptide CGGGAHβDGGR (SEQ ID NO:10) was conjugated to thyroglobulin according to the following directions.

A. Maleimide Thyroglobulin
1. Dissolve 4 mg of thyroglobulin in μl PBS buffer, pH 7.4
2. Add 1 mg Sulfo-SMCC (sulfosuccinimidyl4-N-maleimidomethyl) cyclohexane-1-carboxylate)
3. Incubate for 60 minutes at RT or for 30 minutes at 37° C.
Equilibrate a NAP-5 column with 15 mL PBS buffer, pH 7.4
4. Add 500 μl maleimide activated thyroglobulin to the NAP-5 column
5. Discard the first fraction (500 μl)
6. Add 1000 μl PBS buffer, pH 7.4
7. Collect the next fraction (1000 μl)

B. Conjugation
5 1. Dissolve cys-gly-gly-gly-ala-his-βasp-gly-gly-arg (SEQ ID NO:10) 0.06 mg/ml in PBS buffer, pH 7.4
2. Mix 500 μl cys-gly-gly-ala-his-βasp-gly-gly-arg (SEQ ID NO:10) (0.06 mg/ml) with the maleimide activated thyroglobulin.
3. Incubate at 4° C. for 2 hours or overnight.
Equilibrate a NAP-10 column with 20 mL PBS buffer, pH 7.4
4. Add 1000 μl conjugate to the NAP-10 column
5. Discard the first fraction (1000 μl)
6. Add 1500 μl PBS buffer, pH 7.4
7. Collect the next fraction (1500 μl)
8. Add 15 μl 10%Na-Azide
Store at −20° C.

EXAMPLE 6

CrossLaps ELISA using 6AA linked to Porcine Thyroglobulin

The ISO-ELISA was performed using two different coating conjugates. One coating conjugate, 8AA, was prepared by conjugation of EKAHβDGGR (SEQ ID NO:3) to porcine thyroglobulin using glutaraldehyde. Alternatively, the coating conjugate 6AA was prepared by synthesizing the peptide CGGC-AHβDGGR (SEQ ID NO:10) and subsequently performing site-directed conjugation to porcine thyroglobulin as in Example 5.

Both coating conjugates, i.e., 8AA and 6AA, were used for coating the wells of microtitre plates. Briefly, the coating conjugate was diluted to approx. 200 ng/ml in phosphate buffered saline (PBS), 100 μl was added to the wells of the microtitre plate, and the plates were incubated overnight at 4° C. The plates aspirated, blocked in PBS containing 0.05% Tween 20 and 1% bovine serum albumin (BS) (PBS-T-BSA), and dried. 15 μl of urine sample is mixed with 100 μl of rabbit antiserum diluted approx. 1:20,000 times in PBS-T-BSA (the antiserum was prepared by immunizing rabbits with human bone collagen solubilized by treatment with bacterial collagenase, i.e., CTC) and the mixture is added to the plates. Following incubation for 1 hour at room temperature the plates are washed 3 times with PBST, and subsequently incubated for 1 hour with anti-rabbit immunoglobulin to horse radish peroxidase. After washing 100 μl of substrate solution (TMB) was added, the plates were incubated for 15 minutes, and the color reaction was stopped by addition of an equal volume of diluted sulfuric acid. The absorbency at 450 nm was measured and used for calculation of CrossLaps concentration in the samples. All Cross-Laps values were corrected by creatinine. A standard curve was drawn up based on similar measurements of dilutions of a known concentration of suitable antigen standard. The standard used was a sample of urine from a normal adolescent human in which the concentration of isomerized antigen relative to non-isomerized antigen is at equilibrium.

Relative absorbance was plotted against the concentration of antigen standard using the 6AA coating conjugate and using the 8AA coating conjugate in FIG. 1. The results shown in FIG. 1 indicate that 6AA coating conjugate is preferable to 8AA as the 6AA standard curve is steeper. As a result, for 6AA coating conjugate, any variation in the observed absorbency produces a smaller variation in measured concentration, as compared with 8AA coating conjugate.

The coefficient of variation between repeats was found to be an average of 8.0% for the 6AA based assay but 10.0% for the 8AA based assay. A good correlation was found between measurements of samples using the 6AA kit and similar measurements using the 8AA kit.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of measuring type I collagen degradation products in a body fluid comprising conducting a competition immunoassay in which sample molecules compete with a peptide in binding to an immunological binding partner immunoreactive with the peptide, wherein the peptide consists of the amino acid sequence AHDGGR (SEQ ID NO:2) extended at the N-terminal end with one or more amino acids that do not form a contiguous sequence with AHDGGR (SEQ ID NO:2) in type I collagen.

2. The method of claim 1, wherein said peptide or isomerized peptide is extended at the N-terminal end with four amino acids.

3. The method of claim 1, wherein said four amino acids are CGGG (SEQ ID NO:4) such that said peptide or isomerized peptide has the sequence CGGGAHDGGR (SEQ ID NO:5).

4. The method of claim 1, wherein said immunological binding partner is present in a polyclonal antiserum.

5. The method of claim 1, wherein said immunological binding partner is a monoclonal antibody.

6. The method of claim 5, wherein said monoclonal antibody is raised against an amino acid sequence comprising AHDGGR (SEQ ID NO:2) optionally extended at the N-terminal end with further amino acids.

7. The method of claim 5, wherein said monoclonal antibody has been raised against the amino acid sequence EKAHDGGR (SEQ ID NO:1), wherein D represents aspartic acid or β-aspartic acid.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 8 amino acids
      (B) TYPE: amino acid (C) STRANDEDNESS: unknown
            (D) TOPOLOGY: linear (ii) MOLECULE TYPE: peptide (ix) FEATURE:
            (A) NAME/KEY: Other
            (B) LOCATION: 5
            (D) OTHER INFORMATION: Aspartic Acid or Beta-Aspartic
                Acid (xi) SEQUENCE DESCRIPTION: SEQ ID NO:1:

Glu Lys Ala His Xaa Gly Gly Arg
 1               5

(2) INFORMATION FOR SEQ ID NO:2:

(i) SEQUENCE CHARACTERISTICS:
            (A) LENGTH: 6 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Other
            (B) LOCATION: 3
            (D) OTHER INFORMATION: Aspartic Acid or Beta-Aspartic
                Acid (xi) SEQUENCE DESCRIPTION: SEQ ID NO:2:

Ala His Xaa Gly Gly Arg
 1               5

(2) INFORMATION FOR SEQ ID NO:3:

(i) SEQUENCE CHARACTERISTICS:
            (A) LENGTH: 8 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Other
            (B) LOCATION: 5
            (D) OTHER INFORMATION: Beta-Aspartic Acid (xi) SEQUENCE DESCRIPTION: SEQ ID NO:3:

Glu Lys Ala His Xaa Gly Gly Arg
 1               5

(2) INFORMATION FOR SEQ ID NO:4:

(i) SEQUENCE CHARACTERISTICS:
            (A) LENGTH: 4 amino acids
            (B) TYPE: amino acid
            (C) STRANDEDNESS: unknown
            (D) TOPOLOGY: linear (ii) MOLECULE TYPE: peptide (xi) SEQUENCE DESCRIPTION: SEQ ID NO:4:

Cys Gly Gly Gly
 1

(2) INFORMATION FOR SEQ ID NO:5:

(i) SEQUENCE CHARACTERISTICS:

(A) LENGTH: 10 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Other
            (B) LOCATION: 7
            (D) OTHER INFORMATION: Aspartic Acid or Beta-Aspartic
                Acid (xi) SEQUENCE DESCRIPTION: SEQ ID NO:5:

Cys Gly Gly Gly Ala His Xaa Gly Gly Arg
1               5                   10

(2) INFORMATION FOR SEQ ID NO:6:

(i) SEQUENCE CHARACTERISTICS:
            (A) LENGTH: 7 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Other
            (B) LOCATION: 1
            (D) OTHER INFORMATION: Beta-Aspartic Acid (xi) SEQUENCE DESCRIPTION: SEQ ID NO:6:

Xaa Glu Lys Ser Thr Gly Gly
1               5

(2) INFORMATION FOR SEQ ID NO:7:

(i) SEQUENCE CHARACTERISTICS:
            (A) LENGTH: 8 amino acids
            (B) TYPE: amino acid
            (C) STRANDEDNESS: unknown
            (D) TOPOLOGY: linear (ii) MOLECULE TYPE: peptide (ix) FEATURE:
            (A) NAME/KEY: Other
            (B) LOCATION: 3
            (D) OTHER INFORMATION: Beta-Aspartic Acid (xi) SEQUENCE DESCRIPTION: SEQ ID NO:7:

Gln Tyr Xaa Gly Lys Gly Val Gly
1               5

(2) INFORMATION FOR SEQ ID NO:8:

(i) SEQUENCE CHARACTERISTICS:
            (A) LENGTH: 8 amino acids
            (B) TYPE: amino acid
            (C) STRANDEDNESS: unknown
            (D) TOPOLOGY: linear (ii) MOLECULE TYPE: peptide (xi) SEQUENCE DESCRIPTION: SEQ ID NO:8:

Glu Lys Ala His Asp Gly Gly Arg
1               5

(2) INFORMATION FOR SEQ ID NO:9:

```
        (i) SEQUENCE CHARACTERISTICS:
              (A) LENGTH: 6 amino acids
              (B) TYPE: amino acid
              (C) STRANDEDNESS: unknown
              (D) TOPOLOGY: linear (ii) MOLECULE TYPE: peptide (xi) SEQUENCE DESCRIPTION: SEQ ID NO:9:

Ala His Asp Gly Gly Arg
1               5

(2) INFORMATION FOR SEQ ID NO:10:

(i) SEQUENCE CHARACTERISTICS:
              (A) LENGTH: 10 amino acids
              (B) TYPE: amino acid
              (C) STRANDEDNESS: unknown
              (D) TOPOLOGY: linear (ii) MOLECULE TYPE: peptide (ix) FEATURE:
              (A) NAME/KEY: Other
              (B) LOCATION: 7
              (D) OTHER INFORMATION: Beta-Aspartic Acid (xi) SEQUENCE DESCRIPTION: SEQ ID NO:10:

Cys Gly Gly Gly Ala His Xaa Gly Gly Arg
1               5                   10

(2) INFORMATION FOR SEQ ID NO:11:

(i) SEQUENCE CHARACTERISTICS:
              (A) LENGTH: 6 amino acids
              (B) TYPE: amino acid
              (C) STRANDEDNESS: unknown
              (D) TOPOLOGY: linear (ii) MOLECULE TYPE: peptide (ix) FEATURE:
              (A) NAME/KEY: Other
              (B) LOCATION: 3
              (D) OTHER INFORMATION: Beta-Aspartic Acid (xi) SEQUENCE DESCRIPTION: SEQ ID NO:11:

Ala His Xaa Gly Gly Arg
1               5
```